(12) United States Patent
Hickling (10) Patent No.: US 7,920,709 B1
(45) Date of Patent: Apr. 5, 2011

(54) VECTOR SOUND-INTENSITY PROBES OPERATING IN A HALF-SPACE

(76) Inventor: Robert Hickling, Huntington Woods, MI (US)

( * ) Notice: Subject to any disclaimer, the term of this patent is extended or adjusted under 35 U.S.C. 154(b) by 1158 days.

(21) Appl. No.: 11/607,376

(22) Filed: Dec. 2, 2006

Related U.S. Application Data (63) Continuation-in-part of application No. 10/396,541, filed on Mar. 25, 2003, now Pat. No. 7,058,184, and a continuation-in-part of application No. 10/746,763, filed on Dec. 26, 2003, now Pat. No. 7,054,228, and a continuation-in-part of application No. 10/842,880, filed on May 10, 2004, now Pat. No. 7,054,226, and a continuation-in-part of application No. 11/486,807, filed on Jul. 15, 2006.

(51) Int. Cl.
*H04R 3/00* (2006.01)
*H04R 29/00* (2006.01)
*H04B 17/00* (2006.01)

(52) U.S. Cl. .............................. 381/92; 381/56; 367/13

(58) Field of Classification Search .................... 381/92, 381/56, 58, 122; 73/646, 641; 367/13
See application file for complete search history.

(56) References Cited

U.S. PATENT DOCUMENTS

| 4,236,040 A | 11/1980 | Chung |
| 5,717,656 A * | 2/1998 | Dourbal .................. 367/128 |
| 7,054,226 B1 | 5/2006 | Hickling |
| 7,054,228 B1 | 5/2006 | Hickling |
| 7,058,184 B1 | 6/2006 | Hickling |

OTHER PUBLICATIONS

Suzuki; "Performance Evaluation of a Three-Dimensional Intensity Probe"; J. Acoust. Soc. Jpn (E) 16,4 (1995), 6 pages.*
U.S. Appl. No. 11/486,807, Robert Hickling.

* cited by examiner

*Primary Examiner* — Ping Lee
(74) *Attorney, Agent, or Firm* — Reising Ethington P.C.

(57) ABSTRACT

Method and apparatus (333) for measuring the sound-intensity vector in a half space bounded by a surface such as a wall or the ground (100) using an acoustic vector probe (AVP) (40), where the AVP consists of four small omnidirectional microphones (1, 2, 3 and 4) supported on narrow straight tubes at the vertices of an imaginary regular tetrahedron. The tubes are attached perpendicularly to a ring (42) with the microphones all pointing into the half space. The sound-intensity vector measured by the AVP determines the direction of a sound source within the half space. Interference from echoes caused by reflections from the boundary of the half space and from surrounding objects on the boundary can be reduced by attaching a concave solid structure (55) to the base of the AVP at the supporting ring (42). The inside of the concave structure is lined with absorbing material (65) to reduce interference by reflections from the structure.

13 Claims, 6 Drawing Sheets

VECTOR SOUND-INTENSITY PROBES OPERATING IN A HALF-SPACE

This Application is a Continuation-in-Part of Ser. No. 10/396,541, filed Mar. 25, 2003, now U.S. Patent entitled "Acoustic Measurement Method and Apparatus", U.S. Pat. No. 7,058,184, Jun. 6, 2006, of Ser. No. 10/746,763, filed Dec. 26, 2003, now U.S. Patent entitled "Sound Source Location and Quantification Using Vector Probes" U.S. Pat. No. 7,054,228, May 30, 2006, of Ser. No. 10/842,880, filed May 10, 2004, now U.S. Patent entitled "Method and Apparatus for Echolocation", U.S. Pat. No. 7,054,226, May 30, 2006, and of Continuation-in-Part entitled "Normalizing and Calibrating Microphones in a Sound-Intensity Probe in a Substantially Free Sound Field", Ser. No. 11/486,807, filed 2006, Jul. 15, by Robert Hickling the present inventor.

TECHNICAL FIELD

This invention relates to acoustic vector probes and more specifically to acoustic vector probes designed to measure sound intensity in a half-space.

BACKGROUND OF THE INVENTION

Acoustic Vector Probes

An acoustic vector probe (AVP) measures the sound-intensity vector. The sound-intensity vector is the time average of sound-power flow per unit area and is a non-propagating quantity. Its primary use is to determine the direction of a sound source. Previous AVPs operated in three-dimensional space. However in many applications, an AVP may be located next to a wall or on the ground, so that it has to operate within a half space.

AVPs are described in
1. R. Hickling, 2006, "Acoustic Measurement Method and Apparatus", U.S. Pat. No. 7,058,184, Jun. 6, 2006.

The technical information contained in this patent is hereby incorporated herein by reference. AVPs may consist of a regular tetrahedral arrangement of four omnidirectional microphones. The microphones simultaneously measure the three fundamental quantities of acoustics, namely the sound-intensity and sound-velocity vectors, and sound pressure, at a point. AVPs are more accurate, more compact and less expensive than previous instruments for measuring the sound-intensity vector. AVPs usually measure the sound-intensity vector as a digital Fourier transform (DFT), using the cross-spectral method described in
2. J. Y. Chung, 1980, "Sound Intensity Meter", U.S. Pat. No. 4,236,040, Nov. 25, 1980.

The cross-spectral method provides information about the frequency characteristics of a sound source, enabling the AVP to distinguish one source from another. Sources are also distinguished from one another by how they occur in time.

In using an AVP to determine the direction of a sound source from the sound-intensity vector, it is necessary for the AVP to be omnidirectional, i.e. equally sensitive to sound from all directions. All the microphones in the AVP should be omnidirectional. In addition a procedure for ensuring the AVP itself is omnidirectional and accurate is described in
3. R. Hickling, 2006, "Normalizing and Calibrating the Microphones in a Sound-Intensity Probe in a Substantially Free Field", Patent Application to the United States Patent and Trademark Office, Ser. No. 11/486,807, Filing date, Jul. 15, (2006).

The technical information contained in this application is hereby incorporated herein by reference.

Measurement calculations for the AVP are based on finite-difference approximations that are valid only when the sound wavelength exceeds the microphone spacing according to the relation $kd<1$ where d is the distance between the microphones and $k=2\pi/$wavelength. The condition $kd<1$ places an upper limit on the frequency of the sound-intensity measurement. However it is possible to satisfy this condition by heterodyning higher-frequency measurements to lower frequencies, as described in
4. R. Hickling, 2006, "Method and Apparatus for Echolocation", U.S. Pat. No. 7,054,226, May 30, 2006.

The technical information contained in this patent is hereby incorporated herein by reference.

The use of AVPs to determine the direction, location and strength of a sound source is described in
5. R. Hickling, 2006, "Sound source location and quantification using arrays of vector probes", U.S. Pat. No. 7,054,228, May 30, 2006.

The technical information contained in this patent is hereby incorporated herein by reference.

SUMMARY OF THE INVENTION

The present invention measures the sound-intensity vector using an AVP in a half space. Analog data from the AVP is transmitted to a digital signal processor via an analog-to-digital converter and computed results are presented using a suitable output device.

The acoustic vector probe has four omnidirectional microphones located at the vertices of an imaginary regular tetrahedron with edges of equal length. In the illustrated embodiment, an AVP consists of four omnidirectional microphones positioned at the vertices of an imaginary regular tetrahedron with edges of equal length d. The components of the sound-intensity vector are computed by the signal processor relative to a Cartesian system of coordinates formed by straight lines joining the mid-points of opposite edges of the tetrahedron. The origin of the coordinates is the measurement point of the vector.

The four small omnidirectional microphones of the AVP can be supported by narrow straight tubes that protrude perpendicularly from a ring into the half space, parallel to the axis of the ring. The tubes consist of two pairs, each pair having a particular length, one pair having a length longer than the other by an amount $d/\sqrt{2}$. Each of the pairs of tubes is attached circumferentially at diametrically opposite positions at ninety degree intervals around the ring.

In addition to being omnidirectional, each microphone of the AVP can be normalized with respect to a single omnidirectional comparison microphone, so that all the microphones in the probe have a substantially identical frequency response, thus making the probe itself omnidirectional. To determine the magnitude of the sound intensity vector accurately the single omnidirectional comparison microphone can be a standard microphone with known acoustical characteristics. In the normalization and calibration procedure the lengths of the four narrow straight tubes can be adjusted so that the faces of the four microphones of the AVP and the standard microphone lie in the same plane and exposed to sound from a closely-positioned loudspeaker. When the procedure has been completed the standard microphone is removed and the lengths of the narrow straight tubes can be re-adjusted so that the four microphones of the AVP are again at the vertices of the regular tetrahedron.

The cross-spectral formulation (to be described later) is used to calculate the sound-intensity vector, based on finite-difference approximations. These approximations require that the distance d between microphones satisfies the condition $2\pi d < c/f$, where c is the speed of sound and f is the frequency being measured. The condition $2\pi d < c/f$ places an upper limit on the frequency of the sound-intensity measurement. However the frequency range of the measurement can be extended using a nested arrangement of two or more AVPs with the same coordinate system and measurement point.

Reflections from the surface forming the boundary of the half space and from objects on the surface can be prevented from interfering with measurement of the sound-intensity vector by setting the AVP within a concave solid structure. Interference by reflections from inside the concave structure can be prevented by lining the inside with a sound-absorbing material.

DESCRIPTION OF THE PREFERRED EMBODIMENT

An AVP consisting of four microphones located at the vertices of an imaginary regular tetrahedron, as described earlier, is used to measures the sound-intensity vector in a half space. The sound-intensity vector can determine the direction of a sound source. Methods of normalizing and calibrating the four microphones of the AVP are described. Reflections from the boundary of the half space next to the AVP and from objects on the boundary are prevented from interfering with the sound-intensity measurement by setting the AVP within a concave solid structure. The inner surface of the structure is lined with sound-absorbing material to prevent interference from reflections from the structure.

Figure 1:
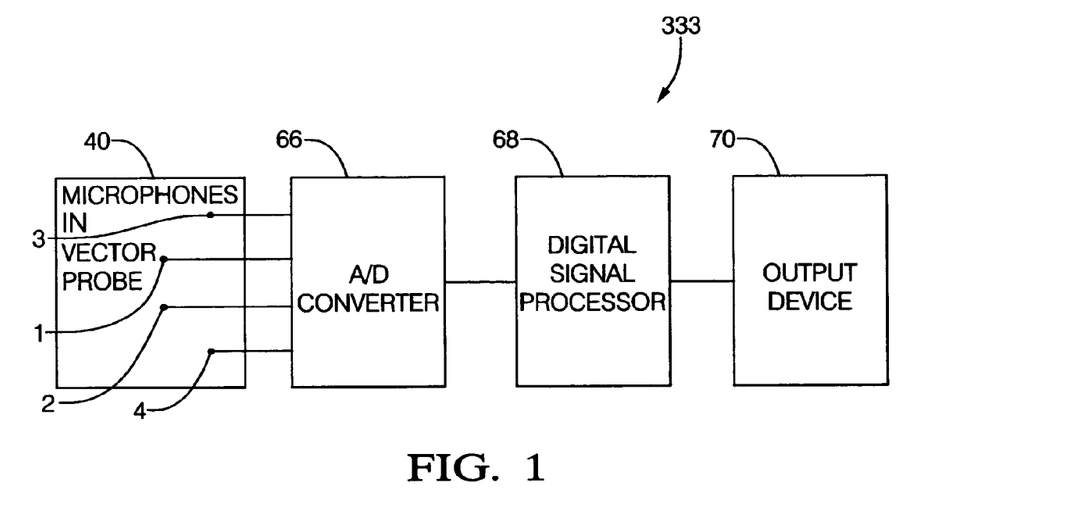
FIG. 1 is a block diagram of an apparatus for obtaining data from an acoustic vector probe (AVP).

FIG. 1 is a block diagram showing the different components of an apparatus 333 for measuring the sound-intensity vector in a half-space. The apparatus includes an acoustic vector probe (AVP) 40, an analog-to-digital converter 66, a digital signal processor 68 and an output device 70. The analog-to-digital converter may be a data acquisition board in the digital signal processor 68 or a chip on the same board as the processor 68. The output device 70 could be a computer screen or a printer.

Figure 2:
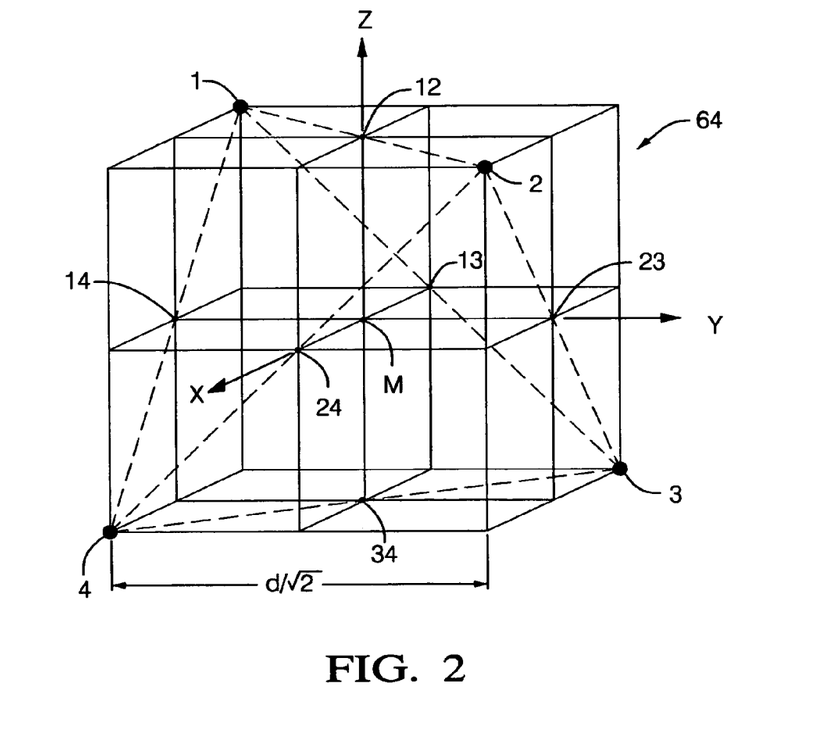
FIG. 2 is a cubic-lattice diagram showing the geometry of the tetrahedral arrangement of microphones in the AVP and the relation of the microphones to the system of Cartesian system of coordinates used in determining the magnitude and direction of the sound-intensity vector at the origin M.

The microphones 1, 2, 3 and 4 of an AVP 40 are positioned at the vertices of a regular tetrahedron, as shown in the lattice diagram in FIG. 2. A regular tetrahedron has edges of equal length d, implying that the microphones 1, 2, 3 and 4 are distance d from each other. The imaginary cubic lattice 64 has 6 faces with midpoints 12, 13, 14, 23, 24, 34. Straight lines joining the midpoints of the opposite faces of the lattice form Cartesian X, Y and Z coordinate axes, with the origin M as the measurement point for determining the sound-intensity vector. The midpoint of the line joining microphones 1 and 2 is a distance $d/\sqrt{2}$ from the midpoint of the line joining microphones 3 and 4.

Figure 3:
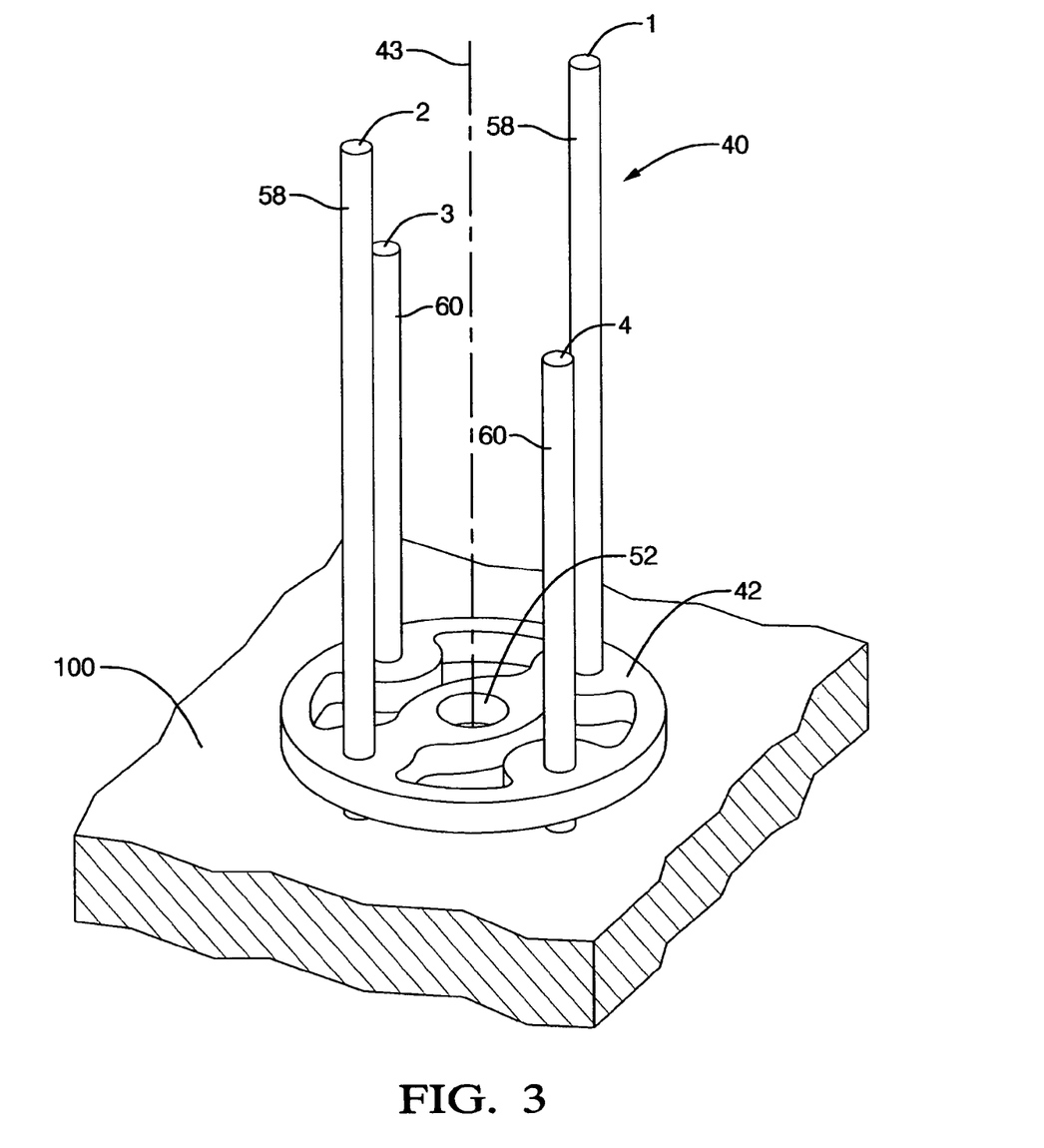
FIG. 3 is a perspective view of an AVP with omnidirectional microphones, located near a wall or the ground, forming a part of the invention.

FIG. 3 is a perspective view of an AVP located near a surface 100, such as a wall or the ground. The microphones 1, 2, 3 and 4 of an AVP are small, sensitive and omnidirectional, such as the FG series manufactured by Knowles Electronics. Members 58 and 60 are supports for the microphones which could be straight narrow tubes that are not necessarily circular in cross-section, protruding perpendicularly from a base fixture which could be a ring 42 having an axis 43 parallel to the tubes. The hole 53 in the fixture can hold a standard omnidirectional microphone with known acoustical characteristics supplied by the manufacturer, which are stored in the digital signal processor 68. The standard microphone is used for normalization and calibration of the microphones 1, 2, 3 and 4 following a procedure described below.

Figure 4:
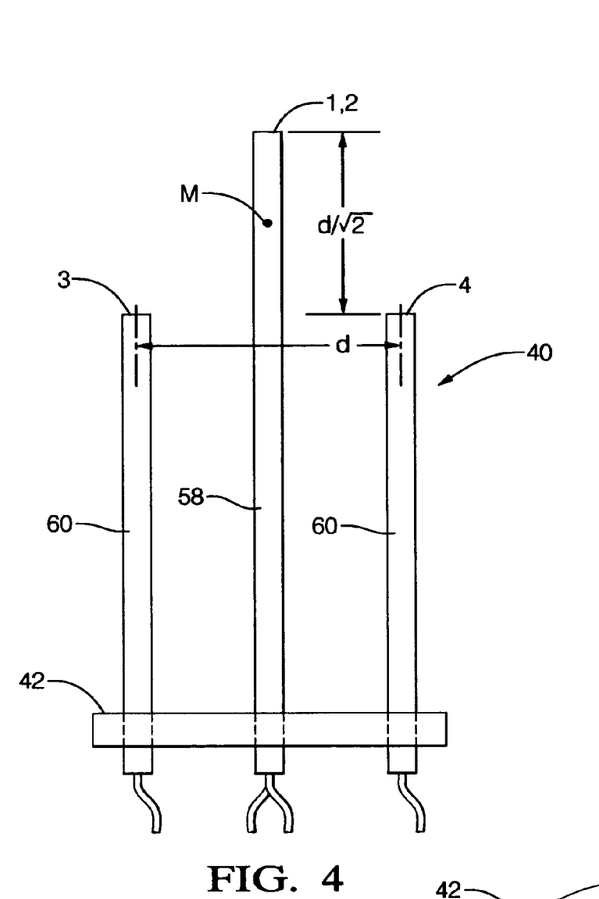
FIG. 4 shows an elevation view of an AVP.
Figure 5:
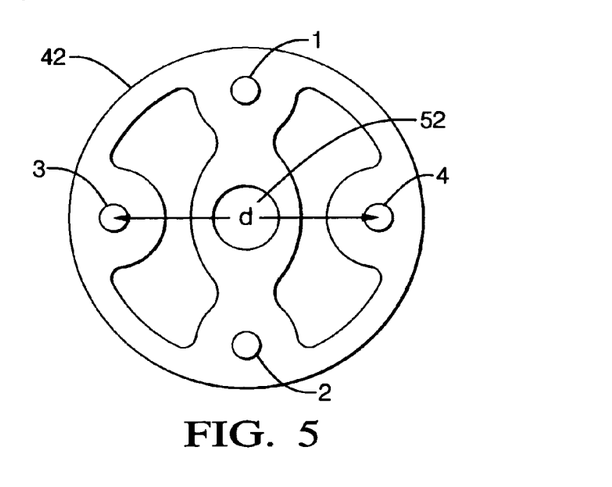
FIG. 5 shows a plan view of an AVP, with a central hole for holding a standard omnidirectional microphone during the normalization and calibration procedure

FIGS. 4 and 5 show elevation and plan views of an AVP and its support structure consisting of a ring 42 with four narrow straight tubes 58 and 60 supporting the microphones of the AVP. The tubes 58 and 60 are in pairs. Each pair has a given length, the length of one pair 60 being shorter than the length of other pair 58. At the ends of the two support tubes 58 are located omnidirectional microphones 1 and 2 and at the ends of the two support tubes 60 are located omnidirectional microphones 3 and 4 corresponding to the vertices of the regular tetrahedron in FIG. 2. The measurement point M is located on the vertical axis 43 of the ring 42 midway between each pair of microphones. The tubes 58 and 60 are spaced diametrically opposite each other circumferentially around the ring at ninety degree intervals.

Figure 6:
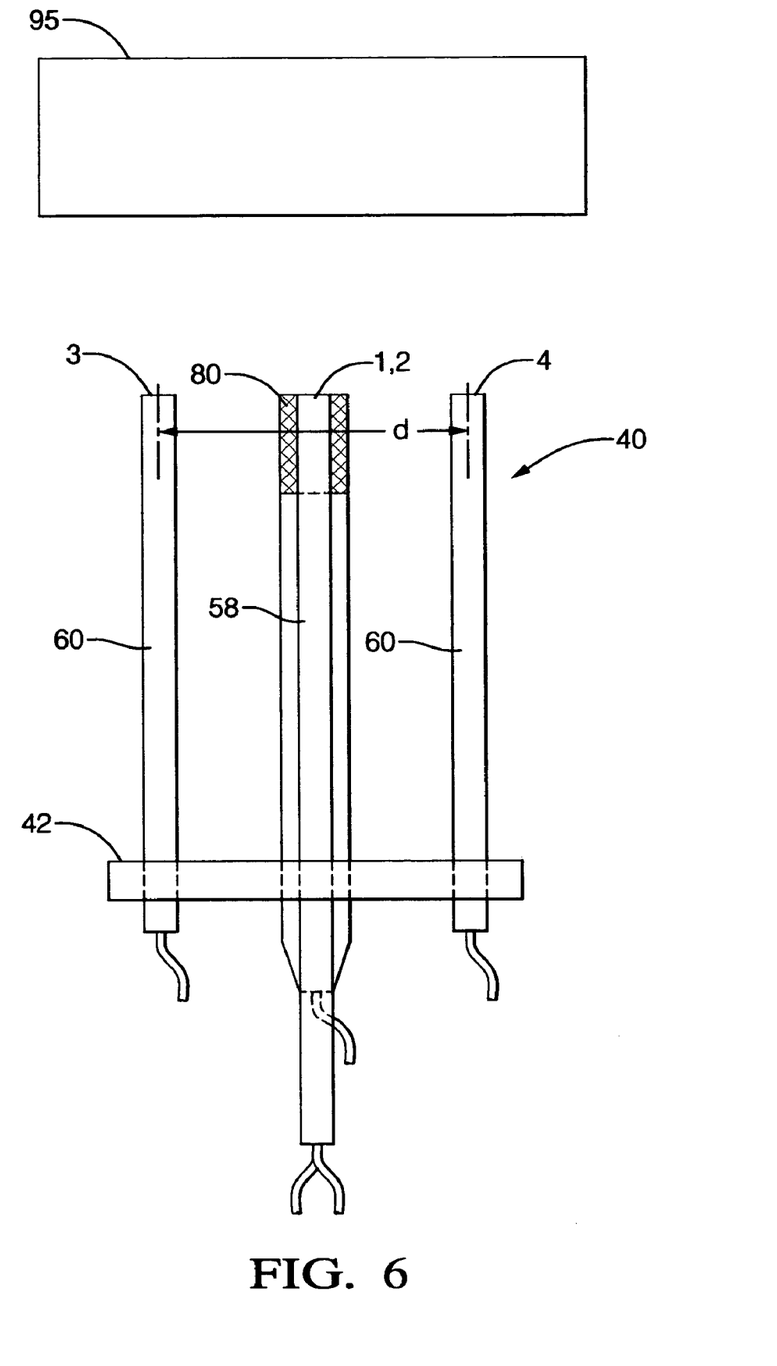
FIG. 6 shows a microphone arrangement for the normalization and calibration procedure.

FIG. 6 shows the adjustments that can be made to the lengths of the tubes so that the omnidirectional microphones 1, 2, 3 and 4 of the AVP 40 lie in a plane together with the standard omnidirectional microphone 80 with known acoustical characteristics. Following the procedure described in Ref. 3, sound from a closely-positioned loudspeaker 95, can be applied to normalize and calibrate the microphones of the AVP 40. Normalizing, based on the use of transfer functions between the standard microphone and the microphones of the AVP 40 (described below), makes the frequency response of the microphones of the AVP 40 substantially the same, thus making the AVP 40 omnidirectional. The known acoustical characteristics of the standard microphone 80 can then be used by the digital signal processor 68 to calibrate the AVP 40.

The use of transfer functions in the normalization and calibration procedure can be described mathematically as follows. Standard DFT (digital Fourier transform) techniques are performed in the microprocessor to determine the transfer function H1C(f) between microphone 1 (for example) and the standard omnidirectional microphone C, as follows $$H1C(f) = G1C(f)/G11(f) \qquad (1)$$

where G1C(f) is the cross-spectrum between the signal at microphone 1 and the standard omnidirectional microphone C, given by $$G1C(f) = FpC(f) \cdot Fp1(f)^* \quad (2)$$

and $G11(f)$ is the auto-spectrum of the signal at microphone 1 given by $$G11(f) = Fp1(f) \cdot Fp1(f)^* \quad (3)$$

where the asterisks denote the complex conjugate. To make the signal $Fp1(f)$ at microphone 1 look like the signal $FpC(f)$ at the calibration microphone C, it is multiplied by the transfer function in Equation (1) to give $$Fp1C(f) = Fp1(f) \cdot H1C(f) \quad (4)$$

The process is repeated for microphone 2 using relations corresponding to Equations (1) through (4) with 2 substituted for 1, as follows $$H2C(f) = G2C(f)/G22(f) \quad (5)$$

where $G2C(f) = FpC(f) \cdot Fp2(f)^* \quad (6)$ and $G22(f) = Fp2(f) \cdot Fp2(f)^* \quad (7)$ To make $Fp2(f)$ look like $FpC(f)$, $Fp2(f)$ is multiplied by the transfer function in Equation (5) to give $$Fp2C(f) = Fp2(f) \cdot H2C(f) \quad (8)$$

Transfer functions for microphones 3 and 4 in the AVP are obtained in the same way. In this way all four microphones in the probe can be made to look like the standard omnidirectional microphone C, making the sensitivity of the probe omnidirectional and calibrating the individual microphones using the known acoustical characteristics of the standard microphone. A similar procedure can be used for the microphones of nested arrangements of AVPs described below. The transfer functions are stored in the signal processor for later use in measurements with the probes.

Figure 7:
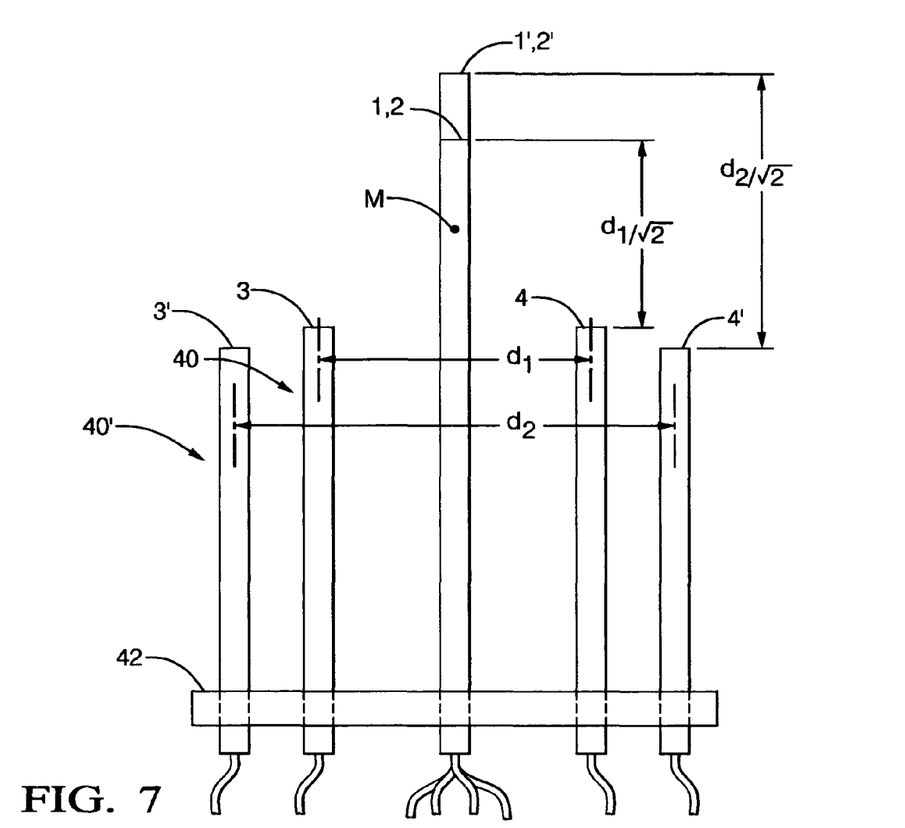
FIG. 7 shows an elevation view of a nested arrangement of two AVPs for extending the frequency range of the measurements.
Figure 8:
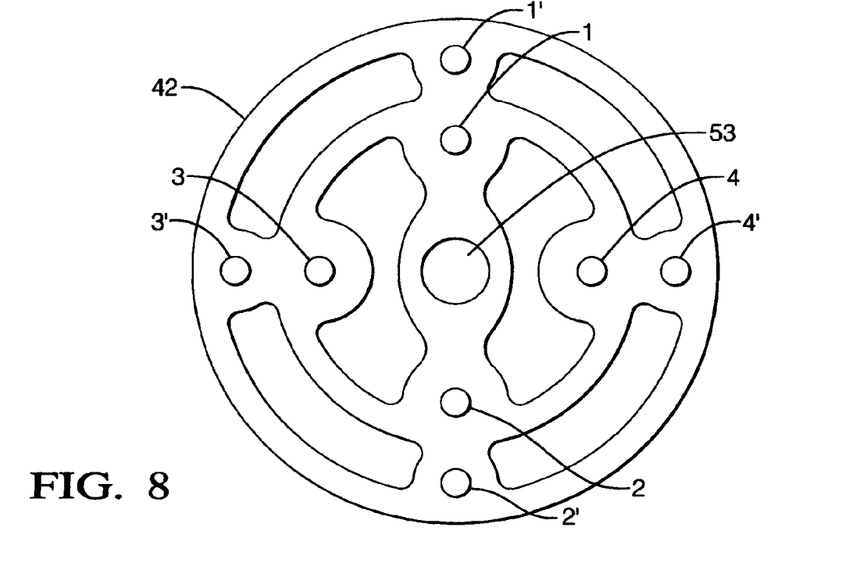
FIG. 8 shows a plan view of the nested arrangement of two AVPs.

FIGS. 7 and 8 show elevation and plan views of a nested arrangement of two AVPs 40 and 40' with spacings $d_1$ and $d_2$ respectively, which extend the frequency range of the vector sound-intensity measurements. The two AVPs have the same Cartesian coordinate axes and measurement point M. According to the condition $2\pi d < c/f$, where c is the speed of sound and f is the frequency being measured, the outer AVP 40' with spacing $d = d_2$ measures more accurately at lower frequencies when f is larger and the inner AVP 40 with spacing $d = d_1$ measures more accurately at higher frequencies when f is smaller. The two sets of measurements are merged over the frequency range by the digital signal processor 68. Nested arrangements can be constructed for more than two AVPs.

Figure 9:
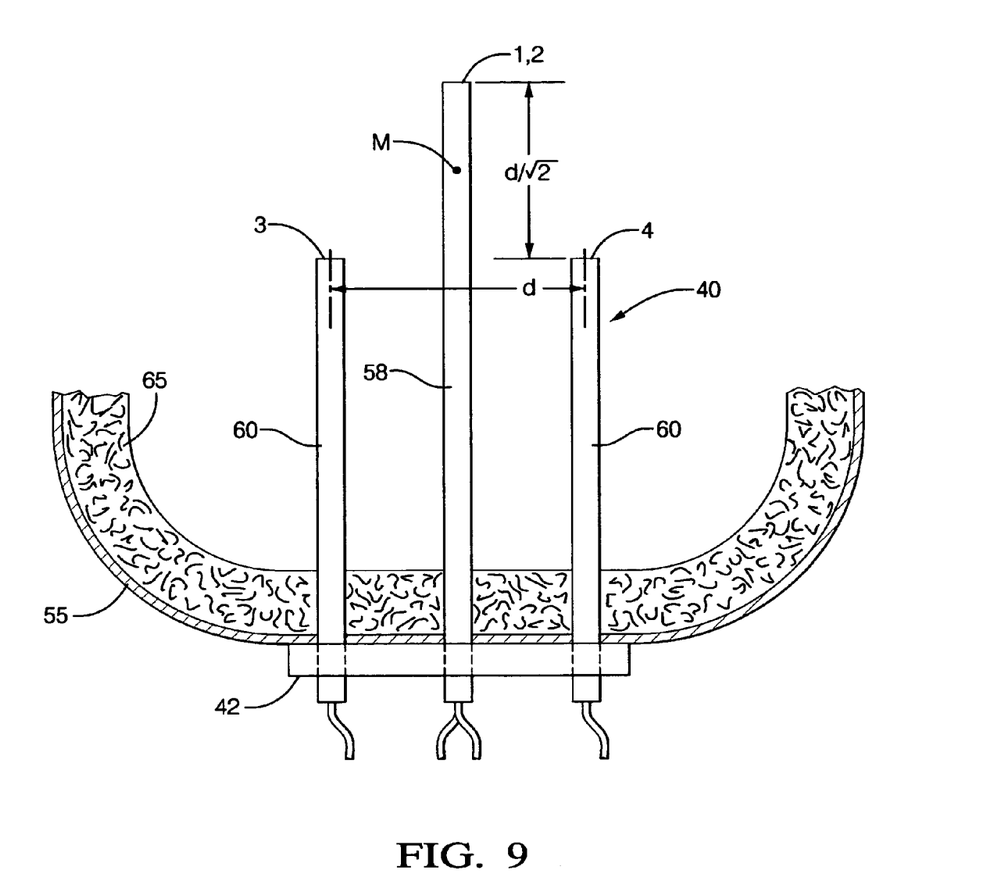
FIG. 9 shows an elevation view of an AVP within a concave structure lined with absorbing material.

It is necessary to prevent sound reflections from interfering with measurements by the AVP 40. FIG. 9 shows an AVP 40 within a concave solid structure 55 whose inner surface is lined with an absorbing layer 65 which could be a porous material such as sponge or cotton fiber. The concave solid structure 55 prevents acoustical reflections from the surface 100 and from nearby objects on the surface from interfering with measurements by the AVP 40. The absorbing layer 65 prevents reflections from the inner surface of the concave solid structure from interfering with the measurements.

Calculations to determine the components of the sound-intensity vector from measurements at the four microphones of the AVP 40 are performed by the signal processor 68. The calculations also determine at the same measurement point, the two other basic quantities of acoustics, namely sound velocity and sound pressure. The mathematics of the calculation method can be described as follows:

At microphones 1, 2, 3 and 4 at the vertices of the regular tetrahedron in FIG. 2, corresponding sound pressures p1, p2, p3 and p4 are digitized using the analog-to-digital converter and recorded in the digital signal processor. The discrete Fourier transforms (DFTs) of the sound pressures are then computed, normalized and calibrated using the transfer-function procedure described above, giving the modified transforms $Fp1(f)$, $Fp2(f)$, $Fp3(f)$ and $Fp4(f)$. For simplicity, the frequency dependence (f) will be dropped. Finite difference approximations (derived from Taylor series expansions) are then applied to obtain the DFTs of the sound pressures at the six midpoints of the edges of the regular tetrahedron at 12, 13, 14, 23, 24 and 34 in FIG. 2, giving respectively $$Fp12 = (Fp1+Fp2)/2 \; Fp13 = (Fp1+Fp3)/2 \; Fp14 = (Fp1+Fp4)/2$$

$$Fp23 = (Fp2+Fp3)/2 \; Fp24 = (Fp2+Fp4)/2 \; Fp34 = (Fp3+Fp4)/2. \quad (9)$$

These approximations are accurate to the second order, i.e. order $(kd)^2/4$, provided.

$$kd/2 < 1 \quad (10)$$

The components of the sound-intensity vector at the measurement point M are determined from the sound pressure DFTs in Equation (9), using the cross-spectral formulation described by Chung in reference 2. The components are $$FIX = -Im\,CS[Fp24, Fp13]/(\rho 2\pi f(d/\sqrt{2}))$$

$$FIY = -Im\,CS[Fp23, Fp14]/(\rho 2\pi f(d/\sqrt{2}))$$

$$FIZ = -Im\,CS[Fp12, Fp34]/(\rho 2\pi f(d/\sqrt{2})) \quad (11)$$

where Im is the imaginary part and CS is the cross spectrum of the sound pressures at the midpoints of the opposite edges of the imaginary regular tetrahedron in FIG. 2, and $\rho$ is the density of the air medium which is approximately 1.2 kg/m³. The amplitude of the sound intensity vector is given by $$FIA = \sqrt{[FIX^2 + FIY^2 + FIZ^2]} \quad (12)$$

expressed in SI units of watts per meter squared.

The classical far field approximation for sound intensity is still widely used and may be employed in the computation as a comparison. This approximation is valid for plane and spherical waves and gives the sound-intensity amplitude as $$FIAff = |FpM|^2/(\rho c) \quad (13)$$

where c is the speed of sound in the fluid medium (approximately 344 m/s for air) and FpM is the finite-difference approximation of the DFT of the sound pressure at the measurement point M given by $$FpM = (Fp1+Fp2+Fp3+Fp4)/4 \quad (14)$$

in SI units of pascals.

The components of the sound-velocity vector are obtained from the finite-difference approximations of the X, Y and Z components of the pressure gradient at the measurement point M, which are $$FDpX = (Fp24 - Fp13)/(d/\sqrt{2})$$

$$FDpY = (Fp23 - Fp14)/(d/\sqrt{2})$$

$$FDpZ = (Fp12 - Fp34)/(d/\sqrt{2}) \quad (15)$$

where again these are accurate to second order. The X, Y and Z components of the DFTs of the sound-velocity vector are then $$FVX = KFDpX$$

$$FVY = KFDpY$$

$$FVZ = KFDpZ \tag{16}$$

where the coefficient $K=i/(\rho 2\pi f)$, i being the square root of $-1$. In SI units these components are in meters per second. The amplitude of each component is given by $$FVXA = |FVX|, FVYA = |FVY| \text{ and } FVZA = |FVZ|.$$

The amplitude of the sound velocity vector is then given by $$FVA = \sqrt{(FVXA^2 + FVYA^2 + FVZA^2)} \tag{17}$$

Unlike the sound-intensity vector, the sound-velocity vector has a 180 degree ambiguity in direction.

The above equations can be developed using software such as LabVIEW and MATLAB and converted into C++ or other suitable computer language for use in the signal processor 68.

While the invention has been described by reference to certain preferred embodiments, it should be understood that numerous changes could be made within the spirit and scope of the inventive concepts described. Accordingly it is intended that the invention not be limited to the disclosed embodiments, but that it have the full scope permitted by the language of the following claims.

I claim:

1. An apparatus which measures the sound-intensity vector in a half space bounded by a surface, the apparatus comprising:
    an acoustic vector probe for determining a sound-intensity vector in three dimensional space in front of said surface;
    said surface being in proximity to said acoustic vector probe to limit sound measurement to said half space bounded by said surface;
    an analog-to-digital converter connected to the acoustic vector probe;
    a digital signal processor receiving input from the analog-to-digital converter and computing the sound-intensity vector measured by said acoustic vector probe;
    an output device for the digital signal processor.

2. The invention as in claim 1, wherein said acoustic vector probe has four omnidirectional microphones located at the vertices of an imaginary regular tetrahedron with edges of equal length.

3. The invention as in claim 2, wherein the components of said sound-intensity vector are computed by said digital signal processor relative to the Cartesian coordinate axes formed by straight lines joining the mid points of opposite edges of the imaginary tetrahedron, the origin of said Cartesian coordinate axes being the measurement point for said sound-intensity vector.

4. The invention as in claim 3, wherein the frequency range of said measurement of said sound-intensity vector is extended using a nested arrangement of two or more of said acoustic vector probes sharing said Cartesian coordinate system with same said measurement point for said sound-intensity vector.

5. The invention as in claim 2, wherein said four omnidirectional microphones are supported at the ends of four tubes that are narrow and straight.

6. The invention as in claim 5, wherein the narrow straight tubes are attached perpendicularly to a ring and protrude from the ring into said half space parallel to the axis of said ring.

7. The invention as in claim 6, wherein said four narrow straight tubes consist of two pairs, each pair of equal length, one pair having a length longer than the other by an amount equal to the length of said edge of said regular tetrahedron, divided by the square root of two.

8. The invention as in claim 7, wherein said lengths of said narrow straight tubes are adjustable relative to said ring so that said four omnidirectional microphones, together with a standard omnidirectional microphone, lie in a plane parallel to said ring.

9. The invention as in claim 8, wherein said omnidirectional microphones of said acoustic vector probe together with the standard omnidirectional microphone are exposed to sound from a closely-positioned loudspeaker, thereby permitting said omnidirectional microphones of said acoustic vector probe to be normalized and calibrated with respect to said standard omnidirectional microphone.

10. The invention as in claim 6, wherein each of said pairs of said narrow straight tubes is attached to said ring at diametrically opposite positions at ninety-degree intervals around said ring.

11. The invention as in claim 6, wherein acoustic interference with measurement of said sound-intensity vector caused by echoes from the boundary of the half space and objects on said boundary is reduced by attaching a solid concave structure to said ring supporting said acoustic vector probe.

12. The invention as in claim 11, wherein the inside of the solid concave structure is lined with sound-absorbing material to prevent interference with said measurement of said sound-intensity vector from echoes from said solid concave structure.

13. A calculation method for acoustic measurement, comprising the steps:
    a. receiving analog sound-pressure signals at the tetrahedral arrangement of four microphones of an acoustic vector probe, said acoustic vector probe having a surface located in proximity behind said microphones to limit sound measurement to a half space in front of said microphones;
    b. simultaneously converting said analog sound-pressure signals into digital form and inputting these signals to a digital signal processor;
    c. computing the discrete Fourier transforms of the pressure signals;
    d. normalizing and calibrating said discrete Fourier transforms in said digital signal processor by multiplying them by said discrete transfer functions as determined by the ensemble averages of the transfer functions between the microphones of said acoustic vector probe and said standard omnidirectional microphone and storing said ensemble averages in the memory of said digital signal processor for use in the measurement calculations;
    e. taking arithmetic averages of said normalized and calibrated pressure signals two microphones at a time in said acoustic vector probe to determine discrete Fourier transforms of the sound pressure at the midpoints of the edges of said tetrahedral arrangement joining each of said two microphones;
    f. calculating the imaginary part of the cross spectra of the discrete Fourier transforms of the sound pressure at opposite midpoints in said tetrahedral arrangement and multiplying by an appropriate factor to obtain the Cartesian components of the discrete Fourier transform of the sound-intensity vector at the measurement point of the said acoustic vector probe;

g. taking the difference between the discrete Fourier transforms between opposite midpoints and dividing by an appropriate factor, to obtain the components of the transforms of the pressure gradient at said measurement point of the probe;
h. multiplying the components of the transforms of the pressure gradient by a conversion coefficient to obtain the components of the discrete Fourier transform of the sound velocity-vector at said measurement point of the probe;
i. summing the normalized and calibrated signals at the four microphones and dividing by four to obtain a transform of the sound pressure at the measurement point of said acoustic vector probe;
j. outputting desired values for sound intensity, velocity and pressure.

* * * * *